US011311561B2

(12) United States Patent
Lee et al.

(10) Patent No.: US 11,311,561 B2
(45) Date of Patent: Apr. 26, 2022

(54) COMPOSITION AND METHOD FOR TREATING, RELIEVING OR PREVENTING NEUROPATHIC PAIN, CONTAINING CHOLINE ALFOSCERATE AS ACTIVE INGREDIENT

(71) Applicant: NANOSTEM CO., LTD., Gyeonggido (KR)

(72) Inventors: Kweon Haeng Lee, Seoul (KR); Jun-Ho Yeo, Gyeonggi-do (KR); Young Lim, Seoul (KR); Kunik Lee, Madison, WI (US); So Hee Hyun, Seoul (KR)

(73) Assignee: Hub Washington Inc., Spokane, WA (US)

( * ) Notice: Subject to any disclaimer, the term of this patent is extended or adjusted under 35 U.S.C. 154(b) by 0 days.

(21) Appl. No.: 16/955,597

(22) PCT Filed: Dec. 10, 2018

(86) PCT No.: PCT/KR2018/015621
§ 371 (c)(1),
(2) Date: Jun. 18, 2020

(87) PCT Pub. No.: WO2019/124842
PCT Pub. Date: Jun. 27, 2019

(65) Prior Publication Data
US 2020/0338099 A1    Oct. 29, 2020

(30) Foreign Application Priority Data

Dec. 19, 2017    (KR) .................. 10-2017-0174814

(51) Int. Cl.
*A61K 31/685*    (2006.01)
*A61P 29/00*    (2006.01)
*A61K 9/00*    (2006.01)

(52) U.S. Cl.
CPC ............ *A61K 31/685* (2013.01); *A61P 29/00* (2018.01); *A61K 9/0019* (2013.01); *A61K 9/0053* (2013.01)

(58) Field of Classification Search
CPC ........................... A61K 31/685; A61K 9/0053
See application file for complete search history.

(56) References Cited

U.S. PATENT DOCUMENTS

| 4,624,946 | A | 11/1986 | Scolastico et al. | |
| 8,633,176 | B2* | 1/2014 | Lee | A61K 9/1694 |
| | | | | 514/131 |
| 2007/0112017 | A1 | 5/2007 | Barlow et al. | |
| 2009/0176740 | A1* | 7/2009 | Phillips, II | A61K 31/4015 |
| | | | | 514/75 |
| 2014/0274957 | A1 | 9/2014 | Driscoll | |
| 2015/0079159 | A1 | 3/2015 | Shankarappa | |
| 2016/0177133 | A1 | 6/2016 | Lim | |

FOREIGN PATENT DOCUMENTS

| EP | 0201623 | 11/1986 |
| JP | 2012-162473 | 8/2012 |
| KR | 1020110106720 | 9/2012 |
| KR | 1020160054216 | 6/2016 |
| KR | 2017-0101081 | 9/2017 |
| KR | 101841654 | 3/2018 |
| KR | 1020140094679 | 8/2019 |

OTHER PUBLICATIONS

Alessandro Bartolini, Lorenzo Di Cesare Mannelli and Carla Ghelardini. Analgesic and Antineuropathic Drugs Acting Through Central Cholinergic Mechanisms: Recent Patents on CNS Drug Discovery, 2011, 6, 119-140. (Year: 2111).*
Google_patents_Jul. 29, 2021_choline_alfoscerate_pain (Year: 2021).*
Google_search_Jul. 29, 2021_acetylcholine_release_promoters_and_neuropathic_pain (Year: 2021).*
SciFinder_search_pain_and_CAS_28319-77-9_Jul. 29, 2021 (Year: 2021).*
Google_scholar_search_Dec. 8, 2021_Glycerophosphorylcholine_and_neuropathy.pdf (Year: 2021).*
Google_search_Dec. 8, 2021_Glycerophosphorylcholine_neuralgia.pdf (Year: 2021).*
Google_search_Dec. 8, 2021_trigeminal_neuralgia_choline.pdf (Year: 2021).*
Gilron et al., "Neuropathic Pain Principles of Diagnosis and Treatment", Mayo Clin Proc, Apr. 2015, pp. 532-545.
Baron et al., "Assessment and diagnosis of neuropathic pain", Curr Opin Support Palliat Care , 2018, vol. 2, pp. 1-8.
Moon, "Neuropathic Pain", Korean journal of health promotion and disease prevention, Oct. 5, 2003, English translation, 11 pages.
Farrar et al., "Clinical importance of changes in chronic pain intensity measured on an 11-point numerical pain rating scale", Pain, 2001, vol. 94, pp. 149-158.
Rowbatham, "What is a 'clinically meaningful' reduction in pain?", Pain, 2001, vol. 94, pp. 131-132.

(Continued)

*Primary Examiner* — Michael P Cohen
(74) *Attorney, Agent, or Firm* — Duane Morris LLP; Gregory M. Lefkowitz; Brandon A. Chan

(57) ABSTRACT

Choline alfoscerate is useful for treating cognitive dysfunction associated with cerebrovascular diseases and degenerative brain diseases. It is a drug with proven safety, which has no effect on the kidney and liver and with no severe side effect reported. When administered to a patient with neuropathic pain, it can significantly reduce the pain intensity and the occurrence of neuropathic pain. Accordingly, it may be used as an active ingredient in a pharmaceutical composition for treating or preventing neuropathic pain and a health functional food composition for improving neuropathic pain and may also be used for a method for treating neuropathic pain by administering choline alfoscerate. In addition, choline alfoscerate may also be used to prepare a medication for treating neuropathic pain.

3 Claims, No Drawings

(56) References Cited

OTHER PUBLICATIONS

Chaplan et al., "Quantitative assessment of tactile allodynia in the rat paw", Journal of Neuroscience Methods, 1994, vol. 53, pp. 55-63.
Guo et al., "Spinal Presynaptic Inhibition in Pain Control", Neuroscience, 2014, vol. 283, pp. 95-106.
Jaggi et al., "Animal models of neuropathic pain", Fundamental & Clinical Pharmacology, 2011, vol. 25, pp. 1-28.
Hawker et al., "Measures of Adult Pain", Arthritis Care & Research, Nov. 2011, vol. 63, No. S11, pp. S240-S252.
DeGrandis, D., et al., "Acetyl-L-Carnitine (Levacecarnine) in the Treatment of Diabetic Neuropathy—A Long-Term, Randomised, Double-Blind, Placebo-Controlled Study," Drugs R&D 2002; 3 (4): 223-231.
Li, S., et al., "Acetyl-L-Carnitine in the Treatment of Peripheral Neuropathic Pain: A Systematic Review and Meta-Analysis of Randomized Controlled Trials," PLoS ONE, 2015, 10(3): e0119479. doi:10.1371/journal.pone.0119479.
Matsubara, K., et al., "The delaying effect of alpha glycerophosphocholine on senescence, transthyretin deposition, and osteoarthritis in senescence-accelerated mouse prone 8 mice," Bioscience, Biotechnology and Biochemistry, 2018, vol. 82., No. 4, pp. 647-653.
English Summary of: Nakagawa, T., et al., "Involvement of spinally—infiltrated immune cells in peripheral nerve injury—induced neuropathic pain: roles of TRPM2," Folia Pharmacol. Jpn., 2013, 142, 215-220.

* cited by examiner

COMPOSITION AND METHOD FOR TREATING, RELIEVING OR PREVENTING NEUROPATHIC PAIN, CONTAINING CHOLINE ALFOSCERATE AS ACTIVE INGREDIENT

CROSS-REFERENCE TO RELATED APPLICATIONS

This application is a § 371 national stage entry of International Application No. PCT/KR2018/015621, filed on Dec. 10, 2018, which claims priority to South Korean Patent Application No. 10-2017-0174814, filed Dec. 19, 2017, the entire contents of which are incorporated herein by reference.

TECHNICAL FIELD

The present disclosure relates to a pharmaceutical composition for treating or preventing neuropathic pain, a health functional food composition for improving neuropathic pain, a method for treating neuropathic pain and a novel use of choline alfoscerate for preparation of a medication for treating neuropathic pain.

BACKGROUND ART

Neuropathic pain is defined by "The International Association for the Study of Pain" as pain caused by a disease or lesion of the somatosensory system. It is distinguished from nociceptive pain. Nociceptive pain is a sort of protective mechanism caused by the activation of nociceptors in response to painful stimuli and is easily controlled by nonsteroidal anti-inflammatory drugs, etc.

In contrast, neuropathic pain is caused by the damage or disorder of the nervous system. Because the causes are very diverse, diagnosis is complicated depending on the causes and treatment is very difficult because it is not treated well with nonsteroidal anti-inflammatory drugs, etc.

Neuropathic pain is largely classified into spontaneous pain, evoked pain and negative symptoms. The spontaneous pain includes the most characteristic symptoms of neuropathy, including paresthesia such as tingling, electric shock-like episodic pain and causalgic pain. The evoked pain includes allodynia caused by non-painful stimuli and hyperalgesia, or increased sensitivity to painful stimuli. The negative symptoms include hypoalgesia, or decreased sensitivity to painful stimuli, and hypoesthesia, or decreased sensitivity to non-painful stimuli (Gilron 2015).

The neuropathic pain is diagnosed by cause analysis, past medical history, physical examination, questionnaires, simple sensory testing, quantitative sensory testing, neurological skin biopsy, electromyography, electroneuronography, drug stress test, MRI, etc. The diagnosis results are used as basic data for treatment (Baron 2008).

Neuropathic pain is treated by non-pharmacological treatment or pharmacological treatment in combination with the removal of the underlying cause. The therapeutic agents for pain treatment should be selected according to the clinical symptoms and pathological cause, not based on the underlying disease.

The non-pharmacological treatment includes sympathetic denervation, surgery, stimulation therapy, physical therapy, psychotherapy, etc. (Dong-eon Moon, 2003).

As therapeutic agents for neuropathic pain, the anticonvulsants pregabalin and gabapentin, the tricyclic antidepressants nortriptyline and desipramine and the serotonin-norepinephrine reuptake inhibitors duloxetine and venlafaxine are used as primary therapeutic agents. Lidocaine patch, capsaicin 8% patch and tramadol are used as secondary therapeutic agents. Occasionally, opioids and botulinum toxin A are used.

Although pregabalin is a medication which is used most frequently and recently as a primary therapeutic agent for neuropathic pain, it is limited in that the administration dosage is restricted for patients with renal failure, it takes time (about 2-8 weeks) until the therapeutic effect is achieved and the cost is relatively high.

Choline, which is a precursor for the neurotransmitter acetylcholine, is one of very useful nutrients necessary for improving brain metabolism or enhancing mental ability. Choline alfoscerate (alpha-GPC), wherein a phospholipid component is bonded to choline, is a semisynthetic derivative of lecithin and is also known as L-alpha glycerylphosphorylcholine. Choline alfoscerate helps the conversion or synthesis of important neurotransmitters in the brain. Specifically, choline alfoscerate is degraded into choline and glycerophosphate after being absorbed in the body and is involved in the production of the neurotransmitter acetylcholine while it passes through the central nervous system (CNS) via the blood-brain barrier (BBB).

Accordingly, it is known that the administration of choline alfoscerate provides therapeutic effect for diseases with the symptoms of decreased neurotransmitters.

At present, choline alfoscerate is useful for treating cognitive dysfunction associated with cerebrovascular diseases and degenerative brain diseases. Especially in Alzheimer's disease, the combined treatment of cholinesterase inhibitor donepezil and choline alfoscerate decreases behavioral and cognitive disturbances more effectively than using donepezil only.

Although many people suffer from neuropathic pain, a therapeutic agent for neuropathic pain which is safe, effective and economical is not available yet. The inventors of the present disclosure have first identified that choline alfoscerate, which has been used to treat cognitive disturbances, exhibits an effect of suppressing neuropathic pain in short time with few side effects and have completed the present disclosure.

REFERENCES OF RELATED ART

Patent Documents (Patent document 1) U.S. Pat. No. 4,624,946.
(Patent document 2) European Patent Registration No. 0,201,623.
(Patent document 3) US Patent Publication No. 2009-0176740.

Non-Patent Documents (Non-patent document 1) Gilron I Baron R, Jensen T. Neuropathic pain: principles of diagnosis and treatment. *Mayo Cin Proc* 90(4):532-545 (2015).
(Non-patent document 2) Baron R, Tolle T R. Assessment and diagnosis of neuropathic pain. *Curr Opin Support Palliat Care* 2:1-8 (2008).
(Non-patent document 3) Dong-eon Moon. 2003 Autumn Conference of Neuropathic pain. Korean Association for Clinical Health Improvement. S245-S252.
(Non-patent document 4) Farrar J T, Young J P, LaMoreaux L, Werth J L, Poole R M. Clinical importance of changes in chronic pain intensity measured on an 11-point numerical pain rating scale. *Pain* 94(2):149-158 (2001).

(Non-patent document 5) Rowbotham M C. What is a "clinically meaningful" reduction in pain?. *Pain* 94(2): 131-132 (2001).

(Non-patent document 6) Hawker G A, Mian A, Kendzerska T, French M. Measures of adult pain. *Arthritis Care Res.* 63(511): S240-5252 (2011).

(Non-patent document 7) Chaplan, S. R., et al., 1994. Quantitative assessment of tactile allodynia in the rat paw. *Journal of Neuroscience Methods,* 53(1), 55-63.

(Non-patent document 8) Guo, D., & Hu, J., 2014. Spinal presynaptic inhibition in pain control. *Neuroscience,* 283, 95-106.

(Non-patent document 9) Jaggi, A. S., Jain, V., & Singh, N., 2011. Animal models of neuropathic pain. *Fundamental and Clinical Pharmacology* 25(1), 1-28.

DISCLOSURE

Technical Problem

The present disclosure is directed to providing a pharmaceutical composition for treating or preventing neuropathic pain, which is capable of treating or preventing neuropathic pain in short time with few side effects.

The present disclosure is also directed to providing a health functional food composition for improving neuropathic pain, which is capable of improving neuropathic pain in short time with few side effects.

The present disclosure is also directed to providing a method for treating neuropathic pain, which is capable of treating neuropathic pain in short time with few side effects.

The present disclosure is also directed to providing a novel use of choline alfoscerate for preparing a medication for treating neuropathic pain.

Technical Solution

The present disclosure relates to a pharmaceutical composition for treating or preventing neuropathic pain, which contains choline alfoscerate as an active ingredient.

The pharmaceutical composition may further contain a pharmaceutically acceptable carrier.

The pharmaceutical composition may be for intravenous administration or oral administration.

The daily administration dosage of the pharmaceutical composition may be 1-400 mg/kg body weight based on choline alfoscerate.

The present disclosure also relates to a health functional food composition for improving neuropathic pain, which contains choline alfoscerate as an active ingredient.

The present disclosure also relates to a method for treating neuropathic pain, which includes administering an effective amount of choline alfoscerate to a patient with neuropathic pain.

In the method for treating neuropathic pain, the administration may be intravenous administration or oral administration.

In the method for treating neuropathic pain, the daily administration dosage may be 1-400 mg/kg body weight based on choline alfoscerate.

The present disclosure also relates to a use of choline alfoscerate for preparing a medication for treating neuropathic pain.

The medication may further contain a pharmaceutically acceptable carrier.

The medication may be for intravenous administration or oral administration.

The daily administration dosage of the medication may be 1-400 mg/kg body weight based on choline alfoscerate.

Advantageous Effects

Choline alfoscerate is useful for treating cognitive dysfunction associated with cerebrovascular diseases and degenerative brain diseases. It is a drug with proven safety, which has no effect on the kidney and liver and with no severe side effect reported. Because it can relieve pain intensity more distinctly and remarkably as compared to nerve block when administered to patients with neuropathic pain such as tingling, hypoesthesia, electric shock-like pain, etc., it can be used as an active ingredient of a pharmaceutical composition for treating or preventing neuropathic pain or a health functional food composition for improving neuropathic pain. In addition, choline alfoscerate may be used in a method for treating neuropathic pain and may also be used to prepare a medication for treating neuropathic pain.

BEST MODE

The present disclosure relates to a pharmaceutical composition for treating or preventing neuropathic pain, which contains choline alfoscerate as an active ingredient.

The present disclosure also relates to a health functional food composition for improving or preventing neuropathic pain, which contains choline alfoscerate as an active ingredient.

*48 The present disclosure also relates to method for treating neuropathic pain by administering an effective amount of choline alfoscerate to a patient with neuropathic pain.

The present disclosure also relates to a use of choline alfoscerate for preparing a medication for treating neuropathic pain.

The pharmaceutical composition for treating or preventing neuropathic pain of the present disclosure may be prepared into a formulation for intravenous administration or oral administration. The formulation may contain a pharmaceutically acceptable carrier commonly used to prepare a pharmaceutical composition.

The carrier may include various compounds or mixtures, including lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc.

For the preparation, a commonly used diluent or excipient such as a filler, an extender, a binder, a humectant, a disintegrant, a surfactant, etc. may be used.

A solid formulation for oral administration may be prepared by mixing the choline alfoscerate with at least one carrier, e.g., starch, calcium carbonate, sucrose, lactose, gelatin, etc. In addition to the simple carriers, a lubricant such as magnesium stearate or talc may also be used.

A liquid formulation for oral administration, which may be a suspension, an internal solution, an emulsion, a syrup, etc., may contain, in addition to commonly used simple diluents such as water or liquid paraffin, various excipients such as a humectant, a sweetener, an aromatic, a preservative, etc.

A formulation for intravenous administration includes a sterilized aqueous solution, a non-aqueous solution, a suspension, an emulsion and a freeze-dried formulation. As the non-aqueous solution or suspension, propylene glycol, polyethylene glycol, a vegetable oil such as olive oil, an injectable ester such as ethyl oleate, etc. may be used.

The administration dosage of the pharmaceutical composition for treating or preventing neuropathic pain of the present disclosure varies depending on the physical condition and body weight of a patient, the severity of a disease, drug type, administration route and administration period but may be determined adequately by those skilled in the art.

In order to achieve the desired effect, the daily administration dosage may be 1-400 mg/kg body weight, specifically 2-200 mg/kg, based on choline alfoscerate. The administration may be made once or several times a day. In addition, the administration may be made periodically over 1-4 weeks. Most specifically, the formulation for oral administration may be administered once or 2-3 times at a daily dosage of 5-200 mg/kg body weight and the formulation for intravenous administration may be administered 1-3 times over 1-4 weeks a daily dosage of 2-50 mg/kg. However, the scope of the present disclosure is not limited by the dosage or frequency of the administration.

The pharmaceutical composition for treating or preventing neuropathic pain of the present disclosure may be administered to mammals including rat, mouse, livestock, human, etc. via various routes. For example, it may be administered orally or via intravenous injection.

The present disclosure also relates to a health functional food composition for improving neuropathic pain, which contains choline alfoscerate as an active ingredient.

When choline alfoscerate is used as an active ingredient of a health functional food, it may be used together with other foods or food ingredients adequately according to common methods. The mixing amount of the active ingredient may be determined adequately depending on purposes such as improvement, prevention, etc.

In general, the health functional food according to the present disclosure may contain choline alfoscerate in an amount of 15 parts by weight or less, specifically 10 parts by weight or less, more specifically 5 parts by weight or less. However, for the purpose of long-term intake for improvement, prevention or health care, the amount may be smaller. In addition, because the safety of choline alfoscerate is proven for long-term oral administration, a larger amount may also be used.

The type of the health functional food is not particularly limited and the choline alfoscerate may be contained in any food in the usual sense, including meat, sausage, bread, chocolate, candies, snacks, confectionery, pizza, instant and other noodles, gums, dairy products including ice creams, soups, beverages, tea, drinks, alcoholic beverages, vitamin complexes, etc.

When the health functional food is in the form of a drink, it may further contain various flavorants or natural carbohydrates as common drinks. The natural carbohydrate may be a monosaccharide such as glucose or fructose, a disaccharide such as maltose or sucrose, a polysaccharide such as dextrin or cyclodextrin or a sugar alcohol such as xylitol, sorbitol, erythritol, etc. As a sweetener, a natural sweetener such as thaumatin or stevia extract, a synthetic sweetener such as saccharin or aspartame, etc. may be used. The content of the natural carbohydrate may be about 0.01-0.04 g, specifically about 0.02-0.03 g, per 100 mL of the drink.

In addition, the health functional food composition for improving neuropathic pain, which contains choline alfoscerate as an active ingredient, may further contain various nutrients, vitamins, electrolytes, flavors, colorants, pectic acid and its salts, alginic acid and its salts, organic acids, protective colloidal thickeners, pH control agents, stabilizers, antiseptics, glycerin, alcohols and carbonating agents used in carbonated drinks. In addition, it may contain a pulp used for preparing natural fruit juice, fruit juice drinks and vegetable drinks. These ingredients may be used either independently or in combination. The content of these additives is usually 0.01-0.1 part by weight based on 100 parts by weight of the composition of the present disclosure, although not being limited thereto.

MODE FOR INVENTION

Hereinafter, the present disclosure will be described in detail through examples. However, the following examples are for illustrative purposes only and it will be apparent to those of ordinary skill in the art that the scope of the present disclosure is not limited by the examples.

I. Clinical Trials

1. Characterization and Classification of Patients

Patients with neuropathic pain were selected as subjects. The patients were asked to report the characteristics of neuropathic pain (type of neuropathic pain, site of occurrence, time of occurrence and frequency of occurrence), causative factors of pain, presence of diseases and relationship with pain, relationship between pain and drug medication, medication of therapeutic agents for pain, etc.

The characteristics of "nerve block treatment group (control group)" patients are described in Table 1, the characteristics of "choline alfoscerate intravenous administration group (Example 1)" patients are described in Table 2 and the characteristics of "choline alfoscerate oral administration group (Example 2)" patients are described in Table 3.

TABLE 1

| Patient number | Gender | Age | Period (years) of neuropathic pain | Site of neuropathic pain | Cause | Symptom |
| --- | --- | --- | --- | --- | --- | --- |
| 1 | M | 73 | 3 | leg | radiculopathy | Tingling |
| 2 | M | 87 | 10 | arm | radiculopathy | Tingling |
| 3 | F | 86 | 10 | leg | radiculopathy | Tingling |
| 4 | M | 35 | 5 | leg | radiculopathy | Tingling |
| 5 | M | 39 | 5 | leg | radiculopathy | Tingling |
| 6 | F | 62 | 5 | leg | radiculopathy | Tingling |
| 7 | F | 52 | 5 | leg | radiculopathy | Tingling |
| 8 | M | 61 | 5 | leg | radiculopathy | Tingling |
| 9 | F | 75 | 10 | leg | radiculopathy | Tingling |
| 10 | F | 75 | 10 | leg | radiculopathy | Tingling |
| 11 | F | 69 | 10 | leg | radiculopathy | Tingling |
| 12 | M | 39 | 4 | leg | radiculopathy | Tingling |

TABLE 1-continued

| Patient number | Gender | Age | Period (years) of neuropathic pain | Site of neuropathic pain | Cause | Symptom |
| --- | --- | --- | --- | --- | --- | --- |
| 13 | M | 56 | 10 | leg | radiculopathy | Tingling |
| 14 | M | 60 | 5 | leg | radiculopathy | Tingling |
| 15 | M | 63 | 10 | hand & foot | radiculopathy | Tingling |
| 16 | M | 73 | 7 | chest | Intercostal neuropathy | Tingling |
| 17 | M | 68 | 5 | leg | radiculopathy | Tingling |
| 18 | F | 48 | 4 | arm | radiculopathy | Tingling |
| 19 | F | 72 | 10 | leg | radiculopathy | Tingling |
| 20 | M | 43 | 5 | leg | radiculopathy | Tingling |
| 21 | M | 58 | 5 | leg | radiculopathy | Tingling |
| 22 | F | 72 | 3 | leg | radiculopathy | Tingling |
| 23 | M | 82 | 10 | leg | radiculopathy | Tingling |
| 24 | M | 61 | 5 | leg | radiculopathy | Tingling |
| 25 | F | 75 | 10 | arm | herpes zoster | Tingling |
| 26 | F | 75 | 10 | leg | radiculopathy | Tingling |
| 27 | F | 69 | 10 | leg | radiculopathy | Tingling |
| 28 | F | 55 | 4 | leg | radiculopathy | Tingling |
| 29 | M | 76 | 10 | leg | radiculopathy | Tingling |
| 30 | M | 70 | 6 | leg | radiculopathy | Tingling |
| 31 | F | 73 | 10 | hand & foot | radiculopathy | Tingling |
| 32 | M | 83 | 7 | chest | Intercostal neuropathy | Tingling |
| 33 | F | 78 | 10 | leg | radiculopathy | Tingling |
| 34 | F | 68 | 5 | leg | radiculopathy | Tingling |
| 35 | M | 76 | 10 | leg | radiculopathy | Tingling |
| 36 | M | 70 | 6 | leg | radiculopathy | Tingling |
| 37 | F | 73 | 10 | hand & foot | radiculopathy | Tingling |
| 38 | M | 68 | 5 | chest | herpes zoster | Tingling |
| Mean ± SD | — | 66.3 ± 13.0 | 7.21 ± 2.65 | — | — | — |

TABLE 2

| Patient number | Gender | Age | Period (years) of neuropathic pain | Site of neuropathic pain | Cause | Symptom |
| --- | --- | --- | --- | --- | --- | --- |
| 1 | F | 69 | 3 | back | diabetes mellitus | skin crawling |
| 2 | M | 61 | 1 | leg | diabetes mellitus | Tingling |
| 3 | F | 54 | 2 | hand | Carpal tunnel syndrome | Tingling |
| 4 | F | 53 | 6 | hand | Carpal tunnel syndrome | Tingling |
| 5 | M | 59 | 2 | foot | radiculopathy | Burning |
| 6 | F | 59 | 3 | leg | radiculopathy | Tingling |
| 7 | M | 57 | 3 | arm | radiculopathy | Tingling |
| 8 | F | 62 | 5 | leg | radiculopathy | Tingling |
| 9 | M | 59 | 5 | leg | radiculopathy | Tingling |
| 10 | F | 77 | 5 | leg | radiculopathy | Tingling |
| 11 | M | 54 | 5 | leg | radiculopathy | Tingling |
| 12 | F | 63 | 4 | leg | diabetes mellitus | Tingling |
| 13 | M | 73 | 5 | leg | radiculopathy | Tingling |
| 14 | M | 72 | 10 | hand & foot | diabetes mellitus | Tingling |
| 15 | F | 64 | 5 | arm | radiculopathy | Tingling |
| 16 | M | 54 | 10 | leg | radiculopathy | Tingling |
| 17 | F | 63 | 5 | leg | radiculopathy | Tingling |
| 18 | M | 57 | 5 | leg | radiculopathy | Tingling |
| 19 | F | 78 | 5 | leg | radiculopathy | Tingling |
| 20 | M | 73 | 7 | leg | radiculopathy | Tingling |
| 21 | M | 48 | 5 | leg | radiculopathy | Tingling |
| 22 | F | 47 | 3 | leg | radiculopathy | Tingling |
| 23 | M | 57 | 5 | leg | radiculopathy | Tingling |
| 24 | F | 71 | 5 | leg | radiculopathy | Tingling |
| 25 | F | 78 | 10 | hand & foot | diabetes mellitus | Tingling |
| 26 | F | 73 | 1 | face | Trigeminal neuralgia | Tingling |

TABLE 2-continued

| Patient number | Gender | Age | Period (years) of neuropathic pain | Site of neuropathic pain | Cause | Symptom |
|---|---|---|---|---|---|---|
| 27 | F | 63 | 10 | leg | diabetes mellitus | Tingling |
| 28 | M | 73 | 5 | leg | radiculopathy | Tingling |
| 29 | M | 72 | 10 | hand & foot | diabetes mellitus | Tingling |
| 30 | F | 64 | 7 | arm | radiculopathy | Tingling |
| 31 | M | 65 | 10 | leg | radiculopathy | Tingling |
| 32 | F | 73 | 7 | leg | radiculopathy | Tingling |
| 33 | M | 77 | 5 | leg | radiculopathy | Tingling |
| 34 | F | 78 | 5 | leg | radiculopathy | Tingling |
| 35 | F | 66 | 4 | leg | diabetes mellitus | Tingling |
| 36 | M | 73 | 5 | leg | radiculopathy | Tingling |
| 37 | M | 72 | 10 | hand & foot | diabetes mellitus | Tingling |
| 38 | F | 63 | 4 | leg | diabetes mellitus | Tingling |
| 39 | M | 73 | 5 | leg | radiculopathy | Tingling |
| 40 | M | 72 | 10 | hand & foot | diabetes mellitus | Tingling |
| 41 | F | 74 | 5 | arm | radiculopathy | Tingling |
| 42 | M | 54 | 10 | leg | radiculopathy | Tingling |
| 43 | F | 63 | 5 | leg | radiculopathy | Tingling |
| 44 | M | 57 | 5 | leg | radiculopathy | Tingling |
| 45 | F | 78 | 5 | leg | radiculopathy | Tingling |
| 46 | M | 73 | 7 | leg | radiculopathy | Tingling |
| 47 | M | 68 | 5 | leg | radiculopathy | Tingling |
| 48 | F | 77 | 3 | leg | radiculopathy | Tingling |
| 49 | M | 76 | 5 | leg | radiculopathy | Tingling |
| 50 | F | 71 | 5 | leg | radiculopathy | Tingling |
| 51 | F | 78 | 10 | hand & foot | diabetes mellitus | Tingling |
| 52 | F | 73 | 1 | arm | herpes zoster | Tingling |
| 53 | F | 65 | 5 | leg | radiculopathy | Tingling |
| 54 | F | 75 | 10 | leg | radiculopathy | Tingling |
| 55 | M | 68 | 7 | leg | radiculopathy | Tingling |
| 56 | F | 66 | 4 | leg | radiculopathy | Tingling |
| 57 | M | 69 | 10 | leg | radiculopathy | Tingling |
| 58 | M | 43 | 3 | arm | radiculopathy | Tingling |
| 59 | F | 66 | 10 | leg | diabetes mellitus | Tingling |
| Mean ± SD | — | 66.3 ± 8.82 | 5.71 ± 2.66 | — | — | — |

TABLE 3

| Patient number | Gender | Age | Period (years) of neuropathic pain | Site of neuropathic pain | Cause | Symptom |
|---|---|---|---|---|---|---|
| 1 | F | 60 | 5 | foot | diabetes mellitus | Stabbing pain |
| 2 | M | 76 | 3 | arm & leg | radiculopathy | Electrical shocks |
| 3 | F | 80 | 10 | leg | radiculopathy | Tingling |
| 4 | F | 68 | 5 | leg | radiculopathy | Tingling |
| 5 | F | 67 | 5 | leg | radiculopathy | Tingling |
| 6 | F | 60 | 5 | leg | radiculopathy | Tingling |
| 7 | M | 68 | 7 | arm | radiculopathy | Electrical shocks |
| 8 | F | 61 | 3 | leg | radiculopathy | Tingling |
| 9 | F | 58 | 3 | leg | radiculopathy | Tingling |
| 10 | F | 60 | 5 | leg | radiculopathy | Tingling |
| 11 | F | 69 | 5 | leg | radiculopathy | Tingling |
| 12 | F | 62 | 10 | leg | diabetes mellitus | Tingling |
| 13 | M | 58 | 5 | leg | radiculopathy | Tingling |
| 14 | F | 65 | 5 | arm & leg | radiculopathy | Tingling |
| 15 | F | 62 | 5 | foot | radiculopathy | Tingling |
| 16 | F | 68 | 10 | foot | radiculopathy | Tingling |
| 17 | F | 55 | 5 | leg | radiculopathy | Tingling |
| 18 | M | 47 | 5 | leg | radiculopathy | Tingling |

TABLE 3-continued

| Patient number | Gender | Age | Period (years) of neuropathic pain | Site of neuropathic pain | Cause | Symptom |
|---|---|---|---|---|---|---|
| 19 | F | 53 | 10 | leg | radiculopathy | Tingling |
| 20 | F | 77 | 5 | leg | radiculopathy | Tingling |
| 21 | F | 79 | 10 | leg | radiculopathy | Tingling |
| 22 | M | 48 | 7 | leg | radiculopathy | Tingling |
| 23 | F | 62 | 10 | leg | radiculopathy | Tingling |
| 24 | F | 87 | 10 | leg | radiculopathy | Tingling |
| 25 | M | 43 | 3 | hand & leg | radiculopathy | Tingling |
| 26 | F | 76 | 7 | leg | diabetes mellitus | Tingling |
| 27 | M | 70 | 10 | foot | diabetes mellitus | Tingling |
| 28 | M | 72 | 2 | arm & leg | radiculopathy | Electrical shocks |
| 29 | F | 75 | 10 | leg | radiculopathy | Tingling |
| 30 | M | 68 | 3 | leg | radiculopathy | Tingling |
| 31 | M | 67 | 5 | leg | radiculopathy | Tingling |
| 32 | F | 65 | 4 | arm | radiculopathy | Tingling |
| 33 | M | 68 | 7 | arm | radiculopathy | Tingling |
| 34 | M | 61 | 3 | leg | radiculopathy | Tingling |
| 35 | F | 57 | 4 | arm | radiculopathy | Tingling |
| 36 | F | 60 | 5 | leg | radiculopathy | Tingling |
| 37 | M | 69 | 3 | leg | radiculopathy | Tingling |
| 38 | M | 81 | 10 | leg | diabetes mellitus | Tingling |
| 39 | M | 68 | 3 | leg | radiculopathy | Tingling |
| 40 | M | 71 | 5 | arm & leg | radiculopathy | Tingling |
| 41 | F | 72 | 5 | leg | radiculopathy | Tingling |
| 42 | F | 73 | 5 | leg | radiculopathy | Tingling |
| 43 | F | 55 | 5 | leg | radiculopathy | Tingling |
| 44 | F | 57 | 3 | leg | radiculopathy | Tingling |
| 45 | F | 53 | 5 | leg | radiculopathy | Tingling |
| 46 | M | 76 | 4 | leg | radiculopathy | Tingling |
| 47 | F | 75 | 10 | leg | radiculopathy | Tingling |
| 48 | M | 58 | 7 | leg | radiculopathy | Tingling |
| 49 | F | 62 | 4 | leg | radiculopathy | Tingling |
| 50 | F | 73 | 10 | leg | radiculopathy | Tingling |
| 51 | M | 53 | 3 | arm & leg | radiculopathy | Tingling |
| 52 | F | 66 | 5 | leg | diabetes mellitus | Tingling |
| 53 | F | 75 | 2 | Chest | herpes zoster | Tingling |
| 54 | M | 68 | 1 | shoulder | herpes zoster | Tingling |
| Mean ± SD | — | 65.5 ± 9.3 | 5.67 ± 2.66 | — | — | — |

The number of the patients was 151, 69 male and 82 female. The average age was 66 and the average period of neuropathic pain was 6 years.

The number of the "nerve block treatment group (control group)" patients was 38, 21 male and 17 female. The average age was 66.3±13.0 years and the average period of neuropathic pain was 7.21±2.65 years. Out of the 38 patients, the neuropathic pain occurred in the upper limbs for 3 people, in the lower limbs for 29 people, in the hand and foot for 3 people, and in the chest for 3 people. Tingling was observed in all 38 people.

The number of the "choline alfoscerate intravenous administration group (Example 1)" patients was 59, 28 male and 31 female. The average age was 66.3±8.82 and the average period of neuropathic pain was 5.71±2.66 years. Out of the 59 patients, the neuropathic pain occurred in the lower limbs for 42 people, in the upper limbs for 6 people, in the hand and foot for 6 people, in the hand for 2 people, in the face for 1 person, in the back for 1 person and in the foot for 1 person. Tingling was observed in 57 people, electric shock-like pain and crawling sensation in 1 person, respectively.

The number of the "choline alfoscerate oral administration group (Example 2)" patients was 54, 20 male and 34 female. The average age was 65.5±9.23 and the average period of neuropathic pain was 5.67±2.66 years. Out of the 54 patients, the neuropathic pain occurred in the lower limbs for 38 people, in the upper limbs and the lower limbs for 5 people, in the upper limbs for 4 people, in the foot for 4 people, in the hand and foot for 1 person, in the chest for 1 person and in the shoulder for 1 person. Tingling was observed in 50 people, electric shock-like pain in 3 people and stabbing sensation in 1 person, respectively.

2. Treatment of Test Groups

The "nerve block treatment group (control group)" patients were injected with 5 mL of 0.5% lidocaine at the sites of pain (4-5 points), once a week.

The "choline alfoscerate intravenous administration group (Example 1)" patients were intravenously injected slowly with choline alfoscerate (1 g/4 mL) mixed in 100 mL of physiological saline, twice a week.

The "choline alfoscerate oral administration group (Example 2)" patients were injected with choline alfoscerate (400 mg/capsule), 3 times a day.

3. Test Method

Pain intensity was measured for 12 weeks. The pain intensity was evaluated according to the 11-point pain intensity numerical rating scale (PI-NRS), where 0=no pain, weakest pain=1 and most severe pain=10. 2-point reduction in the pain intensity was considered clinically significant as reported (Farrar 2001, Rowbotham 2001, Hawker 2011). The pain intensity was measured on the first visit (T0) and was compared with the pain intensity 2 weeks (T1), 4 weeks (T2), 6 weeks (T3), 8 weeks (T4), 10 weeks (T5) and 12 weeks (T6) after the first drug administration.

Statistical analysis was conducted using the SASS package ver. 23 and significance was tested by the paired t-test.

4. Test Result

The therapeutic effect for neuropathic pain for the "nerve block treatment group (control group)", the "choline alfoscerate intravenous administration group (Example 1)" and the "choline alfoscerate oral administration group (Example 2)" is shown in Table 4.

TABLE 4

| Remark | Control group | Example 1 | Example 2 |
|---|---|---|---|
| T0 | 7.00 ± 0.52 | 6.64 ± 1.03 | 6.61 ± 0.83 |
| T1 | 5.39 ± 0.89* | 5.19 ± 1.59* | 5.41 ± 1.16* |
| T2 | 4.66 ± 0.85* | 4.56 ± 1.50* | 4.52 ± 1.42* |
| T3 | 3.63 ± 0.79* | 3.92 ± 1.42* | 3.63 ± 1.45* |
| T4 | 2.87 ± 0.81* | 3.34 ± 1.21* | 3.00 ± 1.23* |
| T5 | 2.37 ± 0.79* | 2.85 ± 1.10* | 2.59 ± 1.13* |
| T6 | 2.24 ± 0.91* | 2.46 ± 0.99* | 2.13 ± 0.99* |

*$P < 0.05$: significant difference in pain intensity before and after treatment The pain intensity decreased significantly for the "nerve block treatment group (control group)", from 7.00 points before drug administration (T0) to 5.39 points at 2 weeks after the first drug administration (T1), by 1.61 points, and to 2.24 points at 12 weeks after the first drug administration (T6), by 4.76 points.

The "choline alfoscerate intravenous administration group (Example 1)" also showed significant decrease in the pain intensity, from 6.64 points before drug administration (T0) to 5.19 points at 2 weeks after the first drug administration (T1), and to 2.46 points at 12 weeks after the first drug administration (T6), by 4.18 points.

The "choline alfoscerate oral administration group (Example 2)" also showed significant decrease in the pain intensity, from 6.61 points before drug administration (T0) to 5.41 points at 2 weeks after the first drug administration (T1), and to 2.13 points at 12 weeks after the first drug administration (T6), by 4.48 points.

The "choline alfoscerate intravenous administration group (Example 1)" and the "choline alfoscerate oral administration group (Example 2) showed significant decrease in the pain intensity of neuropathic pain and some patients reported that the neuropathic pain was decreased the next day after the drug administration.

The "choline alfoscerate intravenous administration group (Example 1)" and the "choline alfoscerate oral administration group (Example 2) showed no side effect after the treatment. Because choline alfoscerate has no effect on the kidney and liver, it is thought that it can be used for people with kidney or liver problems as a therapeutic agent for neuropathic pain.

II. Animal Experiment

The spared nerve injury (SNI) rat model was used as an efficient neuropathic pain model and von Freytest was used for assessing mechanical threshold. The SNI model, one of the peripheral nerve injury models that made from the 3 nerve branches (sciatic nerve), the one was spared, and the other 2 nerves (tibial, common peroneal nerve) were axotomized. Within 4 days of injury, mechanical and thermal hyperalgesia occurs, lasting weeks to up to 6 months.

1. Methods

1) Animals and Treatments

Sprague-Dawley (SD) male rats (Koatech, South Korea) weighing 100-150 g, were used to generate neuropathic pain rat models. The rats were maintained under specifically controlled conditions (ambient temperature 23±2° C., 12-h light/dark cycle). Food pellets (DBL, Chungbuk, South Korea) and water were supplied ad libitum. All procedures complied with Institutional Animal Care and Use Committee of Dankook University (IACUC, South Korea), which adheres to the guidelines issued by the Institution of Laboratory of Animal Resources.

After surgery, rats were divided into three groups: (1) control (0.9% normal saline), (2) pregabalin (30 mg/kg), (3) choline alfoscerate (325 mg/kg).

Four weeks later after surgery, Drugs were injected intraperitoneally once a day for one week.

2) Neuropathic Pain Rat Model

To generate an efficient neuropathic pain model, the rats were anesthetized under 3% isoflurane (Hana Pharm., South Korea), the left calf of the rat leg was incised and the common peroneal and the tibial nerve of three peripheral nerve branches in the sciatic nerve were axotomized and the sural nerve was spared then the surgical site was closed. After the surgery, animals were placed in the home cage to recover. 2 weeks after surgery, hypersensitivity will occur in the lateral area of the rat left hind paw.

3) Von Frey Filament Test 4 weeks later after surgery, we applied von Frey filament test established by 50% up and down threshold method for evaluate mechanical allodynia in SNI model we made (Chaplan et al. 1994). The pain measurement was carried out by three people in order to objectify the results. Rats were habituated 5 minutes in the apparatus. For determining which animal is sensitive to the stimulus, we used 0.4 g, 0.6 g, 1 g, 2 g, 4 g, 6 g, 8 g, 10 g and 15 g of von Frey filament (Stoelting, USA), and excepted animals from the experiment those which do not respond to the stimulus of the filament. We stimulated 5 times in the ventral aspect of rat left paw using each filament from thick to thin. If the rat response to stimulate over 3 times, we considered that the rat has NP. The pain response was determined by the behaviors of the rats suddenly took off their foot and shrank or licked their foot with their tongues. The behavioural patterns of the pain were recorded to calculate the threshold value of the pain.

2. Results

1) Pain Scoring of Mechanical Allodynia 4 weeks after surgery, when the mechanical stimuli were applied to the left paw of rats using von Frey monofilaments, thresholds were calculated by looking at the behavioral patterns. Through this test, the behavioral patterns that appeared when mechanical stimuli were applied to the neuropathic pain model and expressed as threshold which was a qualitative assessment of the pain scoring.

TABLE 5

| Control (g) | | Pregabalin (g) | | Choline alfoscerate (g) | |
|---|---|---|---|---|---|
| Before | After | Before | After | Before | After |
| 2.62 ± 0.72 | 3.74 ± 3.49 | 2.42 ± 0.81 | 9.91 ± 4.12* | 2.59 ± 0.87 | 7.68 ± 4.48* |

*$p < 0.05$ after vs before treatment

Pregabalin produced a significant increment of thresholds (9.91+4.12 g) compared to thresholds before the drug treatment (2.42+0.81 g) ($p<0.05$). Choline alfoscerate also showed a significant increment of thresholds (7.68+4.48 g) before the drug treatment (2.59+0.87 g). Both drugs significantly suppressed mechanical allodynia in the spared nerve injury (SNI) rat model.

Hereinafter, the preparation examples of a pharmaceutical composition for treating or preventing neuropathic pain or a health functional food composition for improving neuropathic pain, which contains choline alfoscerate as an active ingredient, of the present disclosure are described. However, the examples are provided as specific examples only and are not intended to limit the present disclosure.

Preparation Example 1: Preparation of Tablet

| | |
|---|---|
| Choline alfoscerate | 10 mg |
| Corn starch | 100 mg |
| Lactose | 100 mg |
| Magnesium stearate | 2 mg |

After mixing the above ingredients, a tablet was prepared according to a common tablet making method.

Preparation Example 2: Preparation of Capsule

| | |
|---|---|
| Choline alfoscerate | 10 mg |
| Crystalline cellulose | 3 mg |
| Lactose | 14.8 mg |
| Magnesium stearate | 0.2 mg |

After mixing the above ingredients, a capsule was prepared by filling the mixture in a gelatin capsule according to a common method.

Preparation Example 3: Preparation of Injection

| | |
|---|---|
| Choline alfoscerate | 10 mg |
| Mannitol | 180 mg |
| Sterilized distilled water for injection | 2974 mg |
| $Na_2HPO_4 \cdot 12H_2O$ | 26 mg |

An injection was prepared by a common injection preparation method according to the above composition per ampoule.

Preparation Example 4: Preparation of Liquid Formulation

| | |
|---|---|
| Choline alfoscerate | 20 mg |
| High-fructose corn syrup | 10 g |
| Mannitol | 5 g |
| Purified water | adequate |

The above ingredients were dissolved by adding to purified water according to a common liquid formulation preparation method. After adding an adequate amount of lemon flavor, purified water was added to make the total volume 100 mL and the resulting mixture was filled in a brown bottle and then sterilized.

Preparation Example 5: Preparation of Solid-Type Health Functional Food

| | |
|---|---|
| Choline alfoscerate | 100 mg |
| Vitamin mixture | adequate |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Mineral mixture | adequate |
| Ferrous sulfate | 1.75 mg |
| Zinc oxide | 0.82 mg |
| Magnesium carbonate | 25.3 mg |
| Potassium phosphate, monobasic | 15 mg |
| Calcium phosphate, dibasic | 55 mg |
| Potassium citrate | 90 mg |
| Calcium carbonate | 100 mg |
| Magnesium chloride | 24.8 mg |

The above contents of the vitamin and mineral mixtures are given as specific examples relatively suitable for health functional food but may be varied as desired. A health functional food composition was prepared by a common method after mixing the above ingredients and preparing into a granule.

Preparation Example 6: Preparation of Drink-Type Health Functional Food

| | |
|---|---|
| Choline alfoscerate | 100 mg |
| Citric acid | 1,000 mg |
| Oligosaccharide | 100 g |

-continued

| | |
|---|---|
| Plum concentrate | 2 g |
| Taurine | 1 g |
| Purified water | to 900 mL |

According to a common health functional drink preparation method, the above ingredients were mixed and heated at 85° C. for about 1 hour under stirring. The resulting solution was filtered, collected in a sterilized 2-L container and stored in a refrigerator after sealing and sterilization for use in the preparation of the health functional drink of the present disclosure.

INDUSTRIAL APPLICABILITY

Because choline alfoscerate can significantly reduce pain and the occurrence of neuropathic pain when administered to a patient with neuropathic pain, it may be used as an active ingredient in a pharmaceutical composition for treating or preventing neuropathic pain and a health functional food composition for improving neuropathic pain and may also be used for a method for treating neuropathic pain by administering choline alfoscerate. In addition, choline alfoscerate may also be used to prepare a medication for treating neuropathic pain.

The invention claimed is:

1. A method for treating neuropathic pain, wherein the neuropathic pain is caused by radiculopathy, intercostal neuropathy, herpes zoster, diabetes mellitus, carpal tunnel syndrome, or trigeminal neuralgia, comprising administering an effective amount of choline alfoscerate to a patient with neuropathic pain.

2. The method for treating neuropathic pain according to claim 1, wherein the administration is intravenous administration or oral administration.

3. The method for treating neuropathic pain according to claim 1, wherein the daily administration dosage is 1-400 mg/kg body weight based on choline alfoscerate.

* * * * *